US010716639B2

(12) United States Patent
Kapadia et al.

(10) Patent No.: US 10,716,639 B2
(45) Date of Patent: Jul. 21, 2020

(54) MEASURING HEALTH OF A CONNECTOR MEMBER OF A ROBOTIC SURGICAL SYSTEM

(71) Applicant: Covidien LP, Mansfield, MA (US)

(72) Inventors: Jaimeen Kapadia, Cambridge, MA (US); Brian Rockrohr, Guilford, CT (US)

(73) Assignee: Covidien LP, Mansfield, MA (US)

( * ) Notice: Subject to any disclaimer, the term of this patent is extended or adjusted under 35 U.S.C. 154(b) by 191 days.

(21) Appl. No.: 15/548,866

(22) PCT Filed: Mar. 8, 2016

(86) PCT No.: PCT/US2016/021331
§ 371 (c)(1),
(2) Date: Aug. 4, 2017

(87) PCT Pub. No.: WO2016/144937
PCT Pub. Date: Sep. 15, 2016

(65) Prior Publication Data
US 2018/0064498 A1 Mar. 8, 2018

Related U.S. Application Data

(60) Provisional application No. 62/184,305, filed on Jun. 25, 2015, provisional application No. 62/130,672, filed on Mar. 10, 2015.

(51) Int. Cl.
*A61B 34/00* (2016.01)
*A61B 34/30* (2016.01)
(Continued)

(52) U.S. Cl.
CPC .............. *A61B 34/71* (2016.02); *A61B 34/30* (2016.02); *A61B 34/35* (2016.02); *A61B 34/76* (2016.02);
(Continued)

(58) Field of Classification Search
CPC ......... A61B 34/30; A61B 34/35; A61B 34/71; A61B 34/76; A61B 2017/00119;
(Continued)

(56) References Cited

U.S. PATENT DOCUMENTS 5,382,885 A   1/1995   Salcudean et al.
6,206,903 B1 *   3/2001   Ramans ................. A61B 17/29
606/205
(Continued)

FOREIGN PATENT DOCUMENTS

EP          1815949 A1    8/2007
JP      2012235936 A   12/2012
(Continued)

OTHER PUBLICATIONS

International Search Report for (PCT/US2016/021331) date of completion is Jun. 7, 2016 (5 pages).
(Continued)

*Primary Examiner* — Spencer D Patton
(74) *Attorney, Agent, or Firm* — Carter, DeLuca & Farrell LLP

(57) ABSTRACT

A robotic surgical system includes a controller, a surgical instrument supporting an end effector, and one or more connector members coupled to the end effector and movable to operate the end effector. Memory is operably coupled to the controller and is configured to maintain reference data of the one or more connector members. A sensor is secured to the one or more connector members and is disposed in electrical communication with the controller. The sensor is configured to register real-time data of the one or more connector members and communicate the real-time data to the controller. The controller is configured to compare the real-time data to the reference data and provide an output signal in response to a comparison of the real-time data to
(Continued)

the reference data. A pair of connector members may be coupled to the end effector to impart three outputs.

7 Claims, 8 Drawing Sheets

(51) Int. Cl.
    *A61B 34/35*      (2016.01)
    *B25J 9/16*      (2006.01)
    *B25J 13/08*      (2006.01)
    *G01L 5/04*      (2006.01)
    *A61B 90/00*      (2016.01)
    *A61B 17/00*      (2006.01)

(52) U.S. Cl.
    CPC .......... *B25J 9/1694* (2013.01); *B25J 13/085* (2013.01); *G01L 5/04* (2013.01); *A61B 2017/00119* (2013.01); *A61B 2017/00199* (2013.01); *A61B 2017/00398* (2013.01); *A61B 2017/00477* (2013.01); *A61B 2017/00725* (2013.01); *A61B 2034/302* (2016.02); *A61B 2034/715* (2016.02); *A61B 2090/064* (2016.02); *A61B 2090/0803* (2016.02)

(58) Field of Classification Search
    CPC .......... A61B 2017/00199; A61B 2017/00398; A61B 2017/00477; A61B 2017/00725; A61B 2034/302; A61B 2034/715; A61B 2090/064; A61B 2090/0803; B25J 9/1694; B25J 13/085; G01L 5/04
    See application file for complete search history.

(56) References Cited

U.S. PATENT DOCUMENTS

| | | |
|---|---|---|
| 6,436,107 B1 | 8/2002 | Wang et al. |
| 6,969,385 B2 | 11/2005 | Moreyra |
| 7,126,303 B2 | 10/2006 | Farritor et al. |
| 7,204,844 B2 | 4/2007 | Jensen et al. |
| 7,255,263 B2 | 8/2007 | Isaacson et al. |
| 7,752,920 B2 | 7/2010 | Blumenkranz et al. |
| 7,935,130 B2 | 5/2011 | Williams |
| 8,281,670 B2 | 10/2012 | Larkin et al. |
| 8,347,755 B2 | 1/2013 | Bennett et al. |
| 8,347,756 B2 | 1/2013 | Bennett et al. |
| 8,376,934 B2 | 2/2013 | Takahashi et al. |
| 8,479,969 B2 | 7/2013 | Shelton, IV |
| 8,506,555 B2 | 8/2013 | Ruiz Morales |
| 9,788,902 B2 | 10/2017 | Inoue et al. |
| 9,999,477 B2 | 6/2018 | Takahashi et al. |
| 2007/0142969 A1 | 6/2007 | Devengenzo et al. |
| 2007/0151390 A1 | 7/2007 | Blumenkranz et al. |
| 2007/0156285 A1* | 7/2007 | Sillman ............... G16H 40/40 700/245 |
| 2008/0046122 A1 | 2/2008 | Manzo et al. |
| 2009/0248038 A1 | 10/2009 | Blumenkranz et al. |
| 2011/0060346 A1 | 3/2011 | Jensern et al. |
| 2012/0116416 A1 | 5/2012 | Neff et al. |
| 2012/0143211 A1* | 6/2012 | Kishi ..................... A61B 34/30 606/130 |
| 2013/0172713 A1 | 7/2013 | Kirschenman |
| 2015/0018863 A1 | 1/2015 | Brisson et al. |
| 2015/0066050 A1 | 3/2015 | Jardine et al. |
| 2016/0135908 A1* | 5/2016 | Takahashi ............ A61B 34/30 606/130 |

FOREIGN PATENT DOCUMENTS

| | | |
|---|---|---|
| JP | 2015024032 A | 2/2015 |
| WO | 2002/065933 A2 | 8/2002 |
| WO | 2013/043872 A1 | 3/2013 |
| WO | 2015012179 A1 | 1/2015 |

OTHER PUBLICATIONS

Extended European Search Report issued in corresponding European Application No. 16762333.9 dated Feb. 6, 2019.
Chinese Office Action dated Sep. 16, 2019 issued in corresponding CN Appln. No. 2016800139187.
Australian Examination Report dated Oct. 18, 2019 issued in corresponding AU Appln. No. 2016229897.
Japanese Office Action dated Dec. 4, 2019 issued in corresponding JP Appln. No. 2017-545342.

* cited by examiner

MEASURING HEALTH OF A CONNECTOR MEMBER OF A ROBOTIC SURGICAL SYSTEM

CROSS-REFERENCE TO RELATED APPLICATIONS

This application is a U.S. National Stage Application filed under 35 U.S.C. § 371(a) of International Patent Application Serial No. PCT/U.S. 2016/021331, filed Mar. 8, 2016, which claims the benefit of and priority to U.S. Provisional Patent Application Ser. No. 62/184,305, filed Jun. 25, 2015, and U.S. Provisional Patent Application Ser. No. 62/130,672, filed Mar. 10, 2015, the entire disclosures of which are incorporated by reference herein.

TECHNICAL FIELD

The present disclosure relates to robotics, and more specifically to robotic surgical devices and/or systems for performing endoscopic surgical procedures and methods of use thereof.

BACKGROUND

Robotic surgical systems have been used in minimally invasive medical procedures. Although robotic surgical systems provide many benefits such as increased accuracy and expediency, one drawback is a lack of or limited force feedback. Independent of surgical training, force feedback enables more precise dissection with lower applied forces and fewer errors.

Some robotic surgical systems include a console supporting a robot arm, and at least one end effector such as forceps or a grasping tool that is mounted to the robot arm via a wrist assembly. During a medical procedure, the end effector and the wrist assembly are inserted into a small incision (via a cannula) or a natural orifice of a patient to position the end effector at a work site within the body of the patient.

Connector members such as cables extend from the robot console, through the robot arm, and are connected to the wrist assembly and/or end effector. In some instances, the connector members are actuated by means of motors that are controlled by a processing system including a user interface for a surgeon or clinician to be able to control the robotic surgical system including the robot arm, the wrist assembly and/or the end effector.

Generally, these connector members have limited lifespans and a tendency to fail or become un-usable after a certain number of uses, which may vary, depending upon the duration and/or stress each use imposes on these connector members.

SUMMARY

Accordingly, there is a need for robotic surgical systems that provide real-time information regarding connector members for determining health of these connector members and for improving failure prediction accuracy. It would also be desirable to monitor these connector members for establishing force feedback from the end effector. In this regard, a clinician would be able to advantageously determine, for example, grasping forces of the end effector to improve precision and limit errors.

In one aspect, the present disclosure is directed to a robotic surgical system including a controller and a surgical instrument with a shaft assembly supporting an end effector. One or more connector members are coupled to the end effector and movable to operate the end effector. One or more sensors are operably coupled to one or more of the connector members and disposed in electrical communication with the controller for monitoring the connector members.

In one embodiment, the end effector provides a wristed surgical device that uses differential connector member tension on four connector member ends (of two connector members) to drive three primary motion outputs: pitch, yaw, and jaw motion. The connector members may be routed around a set of idler pulleys that pivot about a pitch axis and about another set of idler pulleys that are located proximal to the pitch axis. In some embodiments, all idler pulleys may be located along the shaft assembly. With the jaw and pivot axis coincident and extending through a proximal portion of jaw members of the end effector, this arrangement advantageously provides a short wrist length as compared to devices that provide idler pulleys between the pitch and yaw axes. Pitch, yaw, and grasping/dissecting and any combinations of these motions are achieved through pulling and/or releasing different combinations of the connector member ends.

By comparison to a more traditional end effectors including three closed loop connector members, each of which are positioned for effectuating one of the three outputs (pitch, yaw, and grasp), respectively, the differential drive embodiment is simplified in that it only requires two open looped connector members (four ends) to drive the three outputs (pitch, yaw, and grasp). Further, given that the two connector members of the differential drive embodiment are open looped connector members as compared to the more traditional closed loop three connector member end effectors, the differential drive embodiment provides adjustable connector member tension. More specifically, the tension on the connector members of the differential drive embodiment can be relaxed when the surgical instrument is not in use so as to prevent continuous load on the components (cables, pulleys, tabs, etc.) of the surgical instrument, thereby improving longevity of the surgical instrument and its components. In addition, the open looped connector members enable active monitoring, for example, with the sensors, of output loads, such as grasping force, torque around the pitch axis, and torque around the yaw axis.

Minimized wrist length also advantageously enables greater pitch and/or yaw movement while minimizing instrument shaft motion, which, in turn, enables instruments to be placed closer together and/or enables faster manipulation of the end effector.

The robotic surgical system may include memory operably coupled to the controller and configured to maintain reference data of one or more of the connector members. The reference data can include one or more of: a property of the connector members; a force applied to the connector members; a number of uses of the connector members; or an age of the connector members.

The sensors may be configured to register real-time data of the connector members and communicate the real-time data to the controller. In some embodiments, the sensors include a force sensor, a position sensor, or combinations thereof.

The controller is configured to compare the real-time data to the reference data and provide an output signal in response to a comparison of the real-time data to the reference data. The controller may be operably coupled to one or more motors. The controller can be configured to communicate with the motors to adjust an amount of tension in the connector members in response to the output signal. In some embodiments, the controller is configured to provide the output signal in response to one or more events. The event(s) can include one or more of: a first use of the surgical instrument, a use of the surgical instrument subsequent to the first use of the surgical instrument, a user initiated command, or an expiration of at least one time period.

In some embodiments, the robotic surgical system includes a drive assembly having a drive member and a drive tab supported on the drive member. The drive member is coupled to a motor disposed in electrical communication with the controller. The one or more connector members are secured to an instrument tab. The drive tab and the instrument tab are engagable to manipulate the end effector as the drive tab moves along the drive member in response to actuation of the motor. The drive member and the drive tab may be threadably engaged. The drive member may be rotatable to move the drive tab axially along the drive member.

According to another aspect, a method of determining health of one or more connector members of a robotic surgical system is provided. The connector members are operably coupled to an end effector of the robotic surgical system and movable to operate the end effector. The method includes storing reference data of one or more of the connector members prior to an initial use of one or more of the connector members. The connector members have an initial health. The method includes measuring real-time data of the connector members subsequent to the initial use of one or more the connector members, and comparing the reference data of the connector members with measured real-time data of the connector members to determine the real-time health of the connector members.

In some embodiments, the method involves measuring force applied to the at least one connector members. In certain embodiments, the method includes calibrating tension in the connector members in response to changes in the real-time data of the connector members. The method may involve automating an output signal indicative of real-time data of the connector members in response to one or more events. The method can involve receiving an input signal indicative of a user input to initiate an output signal indicative of real-time data of the connector members. The method can include registering a failure of the connector members and providing an output signal indicative of the failure.

According to yet another aspect, a robotic surgical system includes a controller, a first connector member, a second connector member, an end effector, and one or more motors operably coupled to the controller.

The one or more motors are operably coupled to the first and second connector members and are actuatable to move the first and second connector members.

The end effector includes a first jaw member and a second of jaw member. The first jaw member includes a first jaw pulley and a first grasping portion extending from the first jaw pulley. The first jaw pulley may be integrally formed with the first grasping portion and the second jaw pulley may be integrally formed with the second grasping portion. The second jaw member includes a second jaw pulley and a second grasping portion extending from the second jaw pulley. The first connector member is secured to the first jaw pulley and the second connector member is secured to the second jaw pulley. The first and second connector members are movable to move the first and second jaw members between three different outputs.

In some embodiments, the first and second jaw pulleys are coupled to a clevis mounted to a set of idler pulleys. The first and second connector members are routed around the set of idler pulleys and the first and second jaw pulleys.

The robotic surgical system may include a robotic arm supporting a drive unit. The drive unit includes a drive assembly having one or more drive members and one or more drive tabs supported on the drive members. The drive members are coupled to the motors. One or both of the first and second connector members is secured to one or more instrument tabs. The drive tabs and the instrument tabs are engagable to manipulate the end effector as the drive tabs move along the drive members in response to actuation of the motors. In some embodiments, the drive members and the drive tabs are threadably engaged. The drive members may be rotatable to move the drive tabs axially along the drive members.

Further details and aspects of exemplary embodiments of the present disclosure are described in more detail below with reference to the appended figures.

BRIEF DESCRIPTION OF THE DRAWINGS

Embodiments of the present disclosure are described herein with reference to the accompanying drawings, wherein.

DETAILED DESCRIPTION

Figure 1A:
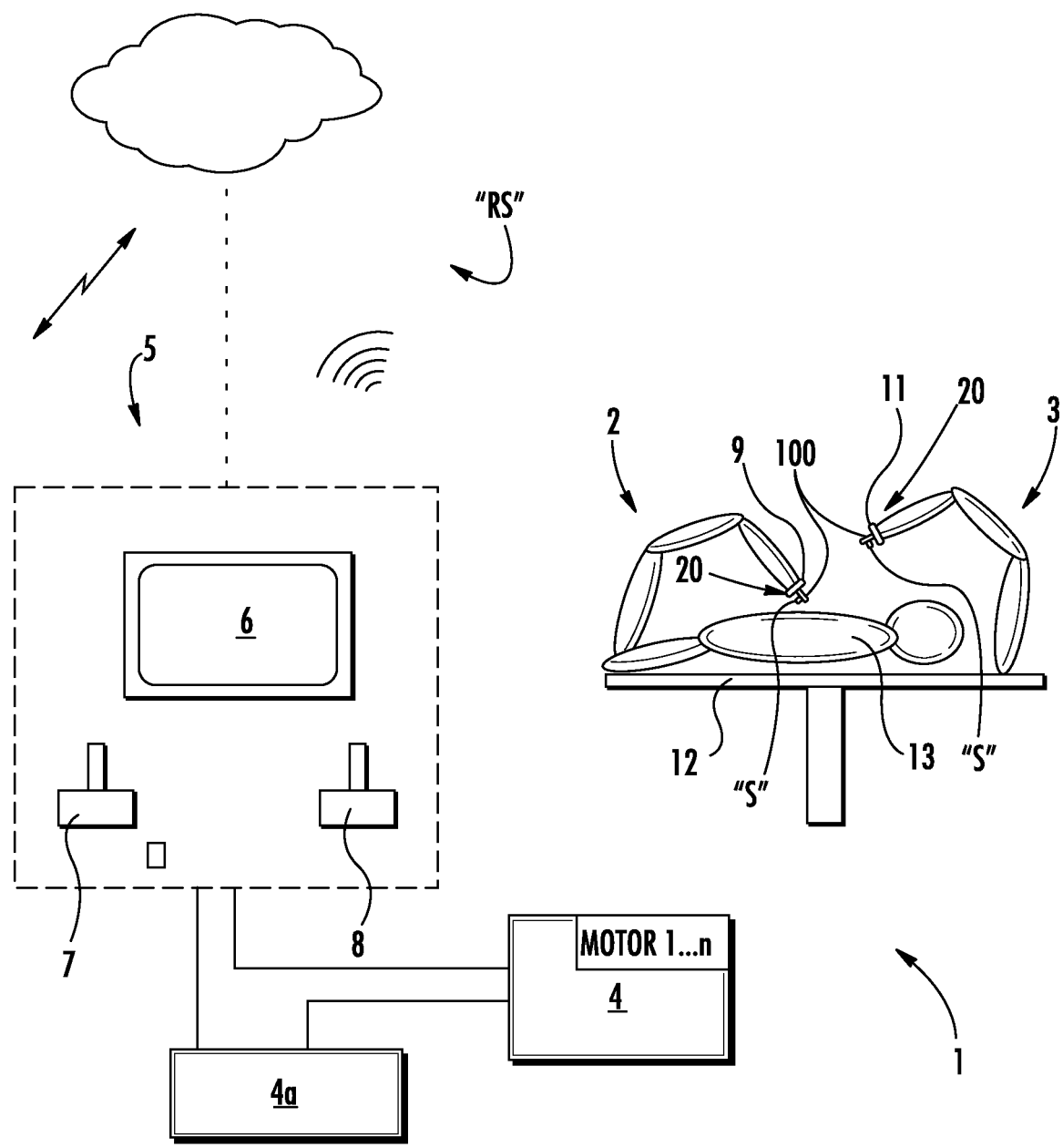
FIG. 1A is a schematic illustration of a medical work station and operating console in accordance with the present disclosure.

Embodiments of the present disclosure are described in detail with reference to the drawings, in which like reference numerals designate identical or corresponding elements in each of the several views.

Referring initially to FIG. 1A, a medical work station is shown generally as work station 1 and generally includes a plurality of robot arms 2, 3; a controller/control device 4; and an operating console 5 coupled with controller 4. Operating console 5 includes a display device 6, which is set up in particular to display three-dimensional images; and manual input devices 7, 8, by means of which a person (not shown), for example a surgeon, is able to telemanipulate robot arms 2, 3 in a first operating mode, as known in principle to a person skilled in the art.

Generally, each of robot arms 2, 3 includes a plurality of members, which are connected through joints, and an attachment device 9, 11, to which may be attached, for example, a surgical tool or surgical instrument 20 supporting an end effector 100.

Work station 1 is configured for use on a patient 13 lying on a patient table 12 to be treated in a minimally invasive manner by means of end effector 100. Work station 1 may also include more than two robot arms 2, 3, the additional robot arms likewise being connected to controller 4 and being telemanipulatable by means of operating console 5. One or more surgical instruments 20 may be attached to the additional robot arm.

Reference may be made to U.S. Patent Publication No. 2012/0116416, filed on Nov. 3, 2011, entitled "Medical Workstation," the entire contents of which are incorporated herein by reference, for a detailed discussion of the construction and operation of work station 1.

Figure 1B:
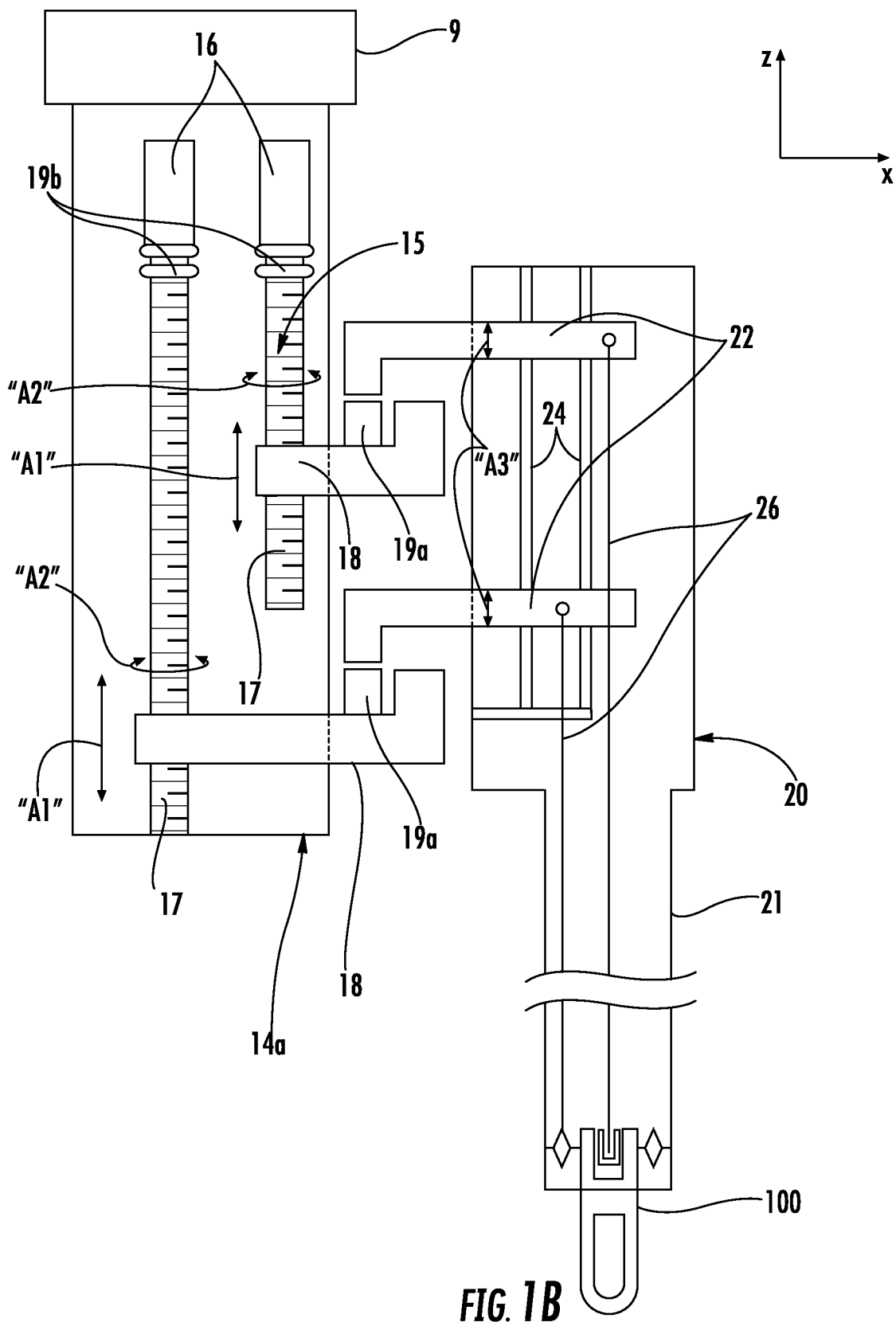
FIG. 1B is a schematic, perspective view of a drive unit and an attaching device coupled to a robot arm of the medical work station of FIG. 1A.

FIG. 1B shows an exemplary attachment device 9 having a drive unit 14 coupled thereto. Drive unit 14 and/or attachment device 9 may be directly and/or indirectly attached to, and/or integrally formed with, one of robot arms 2, 3. For example, in some instances, drive unit 14 is directly attached to one of robot arms 2, 3 and attachment device 9 is indirectly attached to one of robot arm 2, 3 while attachment device 9 is coupled to drive unit 14. In certain instances, attachment device 9 is directly attached to one of the robot arms 2, 3 and drive unit 14 is indirectly attached to robot arm 2, 3 while drive unit 14 is coupled to attachment device 9. In some instances, both attachment device 9 and drive unit 14 are directly attached to one of robot arms 2, 3.

Drive unit 14 includes a drive assembly 15 having one or more motors 16 and one or more drive members 17 coupled to the one or more motors 16. Motor 16 is electrically coupled to controller 4 and operable to impart movement (e.g., rotational movement) to drive member 17. In some embodiments, drive member 17 is a lead screw. One or more drive tabs 18 are mounted to each drive member 17 and movable there along. As illustrated by arrows "A1," drive tab 18 is movable relative drive member 17 in an axially direction (e.g., along the z-axis) in response to rotational movement of drive member 17 in clockwise and/or counterclockwise directions as illustrated by arrows "A2." In some embodiments, drive tab 18 is a split nut drive tab.

Drive tab 18 may be threadably coupled to drive member 17 to effectuate movement of drive tab 18 relative drive member 17. Drive tab 18 and/or drive member 17 may include any suitable threading configuration. For example, one or more of the threads of drive tab 18 and/or drive member 17 can have any suitable shape, diameter, pitch, direction/orientation, etc. In some embodiments, drive member 17 may include multiple sets of threads, each set of threads being threaded in an opposite direction as compared to an adjacent set of threads. In certain embodiments, each set of threads is configured to engage a different drive tab 18 to impart approximating and/or unapproximating movement between multiple drive tabs 18.

Drive tab 18 includes a force sensor 19a (e.g., a transducer or the like) operatively coupled to controller 4 and configured to determine applied force. Drive member 17 supports a position sensor 19b operatively coupled to controller 4 and configured to determine one or more positions of one or more components (e.g., drive tab 18) of drive assembly 15 relative to other components thereof (e.g., drive member 17). For example, position sensor 19b is configured to measure a position and/or movement of output of motor 16, drive member 17, and/or drive tab 18.

As seen in the exemplary embodiment shown in FIG. 1B, drive unit 14 couples to surgical tool 20 (see FIG. 1A) or instrument such as surgical instrument 20. Surgical instrument 20 includes one or more instrument tabs 22 movably mounted on one or more supports or rails 24. For example, instrument tab 22 can be axially movable along rails 24 in the z-direction as indicated by arrows "A3." One or more connector members 26 are coupled to instrument tab 22 that extend along a shaft assembly 21 of surgical instrument 20 to end effector 100 thereof for effectuating movement of end effector 100 and/or portions thereof in response to movement of the one or more connector members 26. Connector members 26 may include cables, rods, etc. Additionally, and/or alternatively, connector members 26 can be moved for imparting forces to end effector 100, for example, to fire end effector (e.g., staples, clips, etc.).

Controller 4 may control current applied to motor 16 during a surgical procedure. The current supplied to motor 16 may be adjusted to move drive member 17 and drive tab 18 so that drive tab 18 pushes against and moves a corresponding instrument tab 22 of surgical instrument 20 in the same z-direction to move a component of surgical instrument 20 such as end effector 100 via connector member 26. In the example shown in FIG. 1B, each connector member 26 in surgical instrument 20 is attached at one end to a respective instrument tab 22 and at an opposite end to a respective portion of end effector 100. Each connector member 26 is connected to a different portion of end effector 100 in order to cause different movements of the end effector 100 (e.g., articulation, rotation, open/close jaw members thereof, etc.) in response to movement of respective instrument tabs 22 via corresponding drive tabs 18 and/or motors 16 of drive unit 14.

Figure 4A:
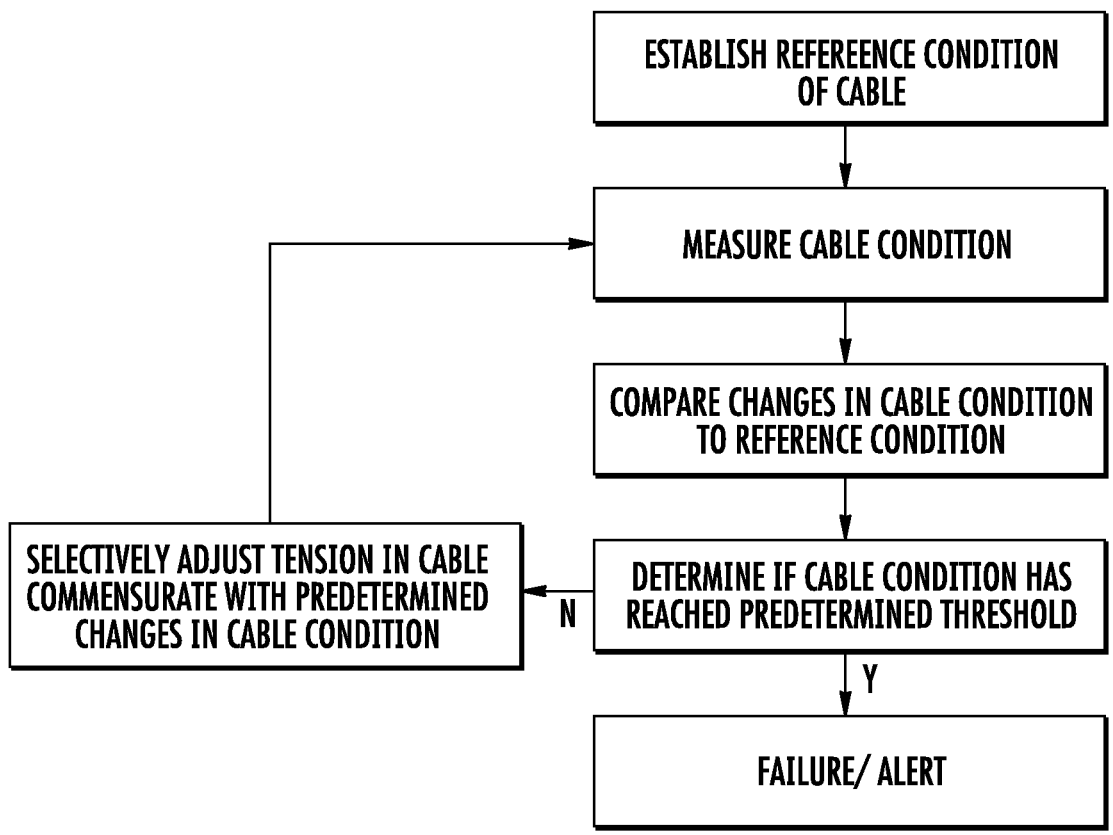
FIG. 4A is a flow chart illustrating a method for maintaining predetermined tension on a connector member of a robotic surgical system.

A method for maintaining predetermined tension on a connector of a robotic surgical system is shown generally in FIG. 4A. Referring also FIG. 1B, the condition of connector member 26 may be measured using data from position sensor 19b and/or force sensor 19a. As part of an initial calibration, motor 16, drive member 17, and/or drive tab 18 may be driven into an initial position. This initial position may be referred to a zero position. Motor 16 may then be actuated to move the output of motor 16, drive member 17, and/or drive tab 18 away from the zero position. Position sensor 19b may measure an amount of movement of the output of motor 16, drive member 17, and/or drive tab 18 away from the zero position. Position sensor 19b may continue to measure this movement at least until force measured at force sensor 19a exceeds a predetermined threshold. When the force measured at force sensor 19a exceeds a predetermined threshold, a total amount of movement from the zero position may be recorded as a reference condition of connector member 26.

The predetermined force threshold may vary in different situations. In some instances, the predetermined force threshold may be a fixed value that is not customized for different applications. In other instances, the predetermined force may vary for different surgical instruments. For example, the predetermined force may be selected to correspond to an amount of force needed to be applied on instrument tab 22 to fully tension connector member 26 without moving a component coupled thereto (such as end effector 100). In other instances, different criteria may be used to select the predetermined force.

Once the reference condition of connector member 26 is the determined, subsequent changes in condition of connector member 26 may be compared to the reference condition. To measure subsequent changes in the connector member 26 condition, the output of motor 16, drive member 17, and/or drive tab 18 may be moved into the zero position. Motor 16 may then be actuated to move the output of motor 16, drive member 17, and/or drive tab 18 away from the zero position. Position sensor 19b may measure an amount of movement of the output of motor 16, drive member 17, and/or drive tab 18 away from the zero position. Position sensor 19b may continue to measure the movement at least until the force measured at force sensor 19a exceeds a predetermined threshold. When the force measured at force sensor 19a exceeds a predetermined threshold, the total amount of movement from the zero position may be recorded as an updated condition of connector member 26. The updated condition of connector member 26 may then be compared to the reference condition of connector member 26 to identify a change in the condition of connector member 26.

Connector member 26 may stretch out under high tension or otherwise deform over time as connector member 26 is used. As connector member 26 stretches out or otherwise deforms, the distances that drive tab 18 and instrument tab 22 may need to be moved to set a particular connector member 26 tension in connector member 26 corresponding to the predetermined threshold measured at force sensor 19a may also change. The greater the deformity in connector member 26, the more drive tab 18 and instrument tab 22 may need to be moved. If the position in the updated condition differs from that in the reference condition by more than a predetermined amount, then different actions may be taken. In some instances, if identified change in the condition of connector member 26 exceeds a threshold then an initial indication may presented to alert a person that connector member 26 may need to be replaced. In some instances, if the change in condition exceeds a second threshold then the work station 1 may indicate that the connector member life has been exceeded and/or prevent the use of the surgical instrument 20 containing connector member 26. In certain instances, the updated condition and/or reference condition may be compared to a set of known values to identify an estimated remaining useful life/health of connector member 26. In some instances, dates that the updated condition and the reference condition were measured along with recorded values of the updated condition and reference condition may be compared to a set of known values to identify an estimated end of life date for replacing connector member 26. In certain instances, different actions and/or two or more of the aforementioned actions may be taken.

Figure 2:
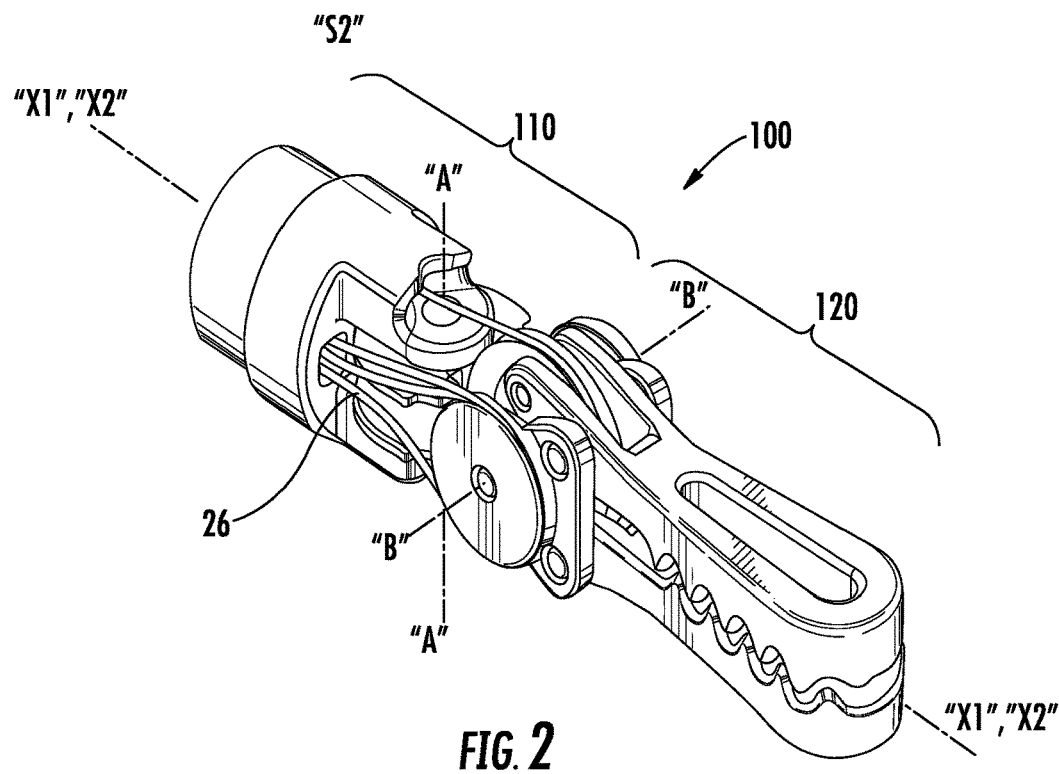
FIG. 2 is a perspective view of an end effector, according to an embodiment of the present disclosure, for use in the medical work station of FIG. 1A, illustrating a jaw assembly thereof in a closed condition.
Figure 3:
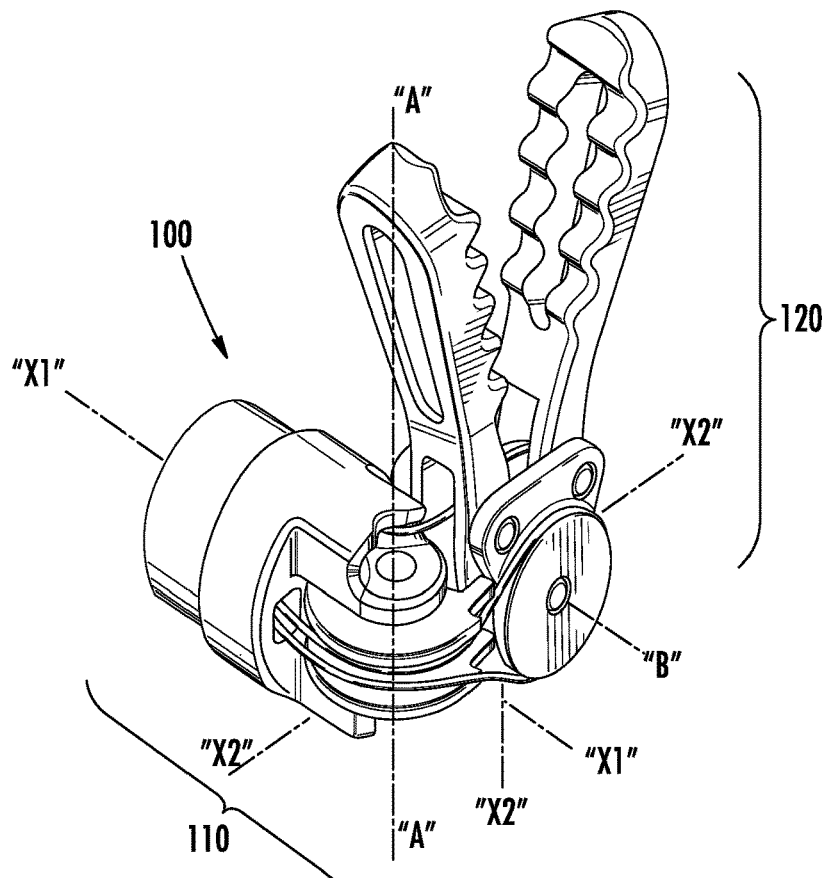
FIG. 3 is a perspective view of the end effector of FIG. 2 illustrating the jaw assembly thereof in an open and articulated condition, and illustrating a wrist assembly thereof in an articulated condition.

As seen in FIGS. 2 and 3, end effector 100 can include a jaw assembly 120 connected to a wrist assembly 110 and one or more connector members 26 for moving (e.g. pivoting/articulating/rotating/opening/closing) jaw assembly 120 about/relative to longitudinal axes such as long axes "X1-X1" and/or "X2-X2" and/or about/relative to pivot axes such as pivot axes "A-A" and/or "B-B." Wrist assembly 110 couples jaw assembly 120 to a robot arm such as robot arms 2, 3.

Reference may be made to International Application No. PCT/U.S. 2014/61329, filed on Oct. 20, 2014, entitled "Wrist and Jaw Assemblies for Robotic Surgical Systems," the entire content of which is incorporated herein by reference, for a detailed discussion of the construction and operation of end effector 100.

In use, as connector members 26 are moved, connector members 26 effect operation and/or movement of each end effector 100 of the surgical instrument (see, e.g., FIGS. 2 and 3). It is contemplated that controller 4 activates the various motors 16 to move a respective connector member 26 via tabs 22 in order to coordinate an operation and/or movement of one or more end effectors 100. Although FIG. 1B shows one end of connector member 26 that is coupled to instrument tab 18 and another end coupled to end effector 100, in some instances two or more connector members 26 or two ends of a single connector member may be coupled to instrument tab 22. For example, in some instances, two connector members or connector member ends may be coupled in opposite directions to a single motor so that as the motor is activated in a first direction, one of the connector members winds up while the other connector member lets out. Other connector member configurations may be used in different embodiments.

Additionally, while FIG. 1B shows drive tab 18 engaging with instrument tab 22 only on an upper side of drive tab 18 as drive tab 18 moves up a length of drive member 17, other variations are also possible. In some instances, drive tab 18 may engage with instrument tab 22 on more than one side (e.g., a top and bottom side) and/or instrument tab 22 may engage with drive tab 18 on more than one side. Having at least one of the tabs 18, 22 engage with the other on more than one side may ensure that the tabs 18, 22 are locked together so that when drive tab 18 moves up, instrument tab 22 also moves up, and when drive tab 18 moves down, then instrument tab 22 also moves down.

Referring again to FIG. 1A, robot arms 2, 3 may be driven by electric drives (not shown) that are connected to controller 4. Controller 4 (e.g., a computer) is set up to activate the drives, in particular by means of a computer program, in such a way that robot arms 2, 3, their attachment devices 9, 11, and thus, surgical instrument 20 (including end effector 100) execute a desired movement according to a movement defined by means of manual input devices 7, 8. Controller 4 may also be set up in such a way that it regulates the movement of robot arms 2, 3 and/or of the drives.

Controller 4 can include any suitable logic control circuit adapted to perform calculations and/or operate according to a set of instructions. Controller 4 can be configured to communicate with a remote system "RS," wirelessly (e.g., Wi-Fi, Bluetooth, LTE, etc.) and/or wired. Remote system "RS" can include data, instructions and/or information related to the various components, algorithms, and/or operations of work station 1. Remote system "RS" can include any suitable electronic service, database, platform, cloud, or the like. Controller 4 may include a central processing unit operably connected to memory. The memory may include transitory type memory (e.g., RAM) and/or non-transitory type memory (e.g., flash media, disk media, etc.). In some embodiments, the memory is part of, and/or operably coupled to, remote system "RS."

Controller 4 can include one or more counters to count, for example, a number of uses of one or more of the components of the medical work station (e.g., connector members 26, end effector 100, etc.). Controller 4 can include a plurality of inputs and outputs for interfacing with the components of work station 1, such as through a driver circuit. Controller 4 can be configured to receive input signals and/or generate output signals to control one or more of the various components (e.g., one or more motors 16) of work station 1. The output signals can include, and/or can be based upon, algorithmic instructions which may be pre-programmed and/or input by a user. Controller 4 can be configured to accept a plurality of user inputs from a user interface (e.g., switches, buttons, touch screen, etc. of operating console 5) which may be coupled to remote system "RS."

A database 4a can be directly and/or indirectly coupled to controller 4. Database 4a can be configured to store pre-operative data from living being(s) 13 and/or anatomical atlas(es). Database 4a can include memory which can be part of, and/or or operatively coupled to, remote system "RS."

In some embodiments, the memory of database 4a (or the like) includes reference data of one or more of any of the components of work station 1. In some embodiments, the reference data can be predetermined. In certain embodiments, the reference data can be measured, created, or stored in real-time. The reference data can include any suitable property, characteristic and/or condition of one or more of the components of work station 1. For example, the memory can include tensile data of the one or more connector members 26 such as connector member strength, elasticity, and/or degradation data applicable to one or more of connector members 26, a number of uses of one or more of connector members 26, and/or an age of one or more of connector members 26. In some embodiments, the reference data may include ranges or sets of ranges to which real-time data can be compared and contrasted for determining health (e.g., expended and/or remaining lifespan). The memory of database 4a may also store a connector member reference condition, one or more updated connector member conditions, and/or other data associated with the stored conditions, such as a date that the condition was measured, created, or stored.

The work station 1 may support one or more position sensors 19b and force sensors 19a that may be in electrical communication with controller 4 and/or remote system "RS." The sensors 19a, 19b may be configured to provide an input signal indicative of real-time position and force data to controller 4. Force sensor 19a may include a strain gauge load cell and/or a piezoelectric load cell. Position sensor 19b may include an absolute or incremental position sensor. In some instances, where positional sensor is configured to measure position information of a rotating object, such as drive member 17 and/or a shaft output of motor 16, position sensor 19b may include a rotary encoder or other sensor that converts an angular position or motion of a rotating output to an analog or digital code. Sensors 19a, 19b may be configured to measure, sample, and/or transmit positional or force information in real-time at similar intervals so that the data from each of the sensors 19a, 19b coincides with each other.

Controller 4 can be programmed to compare real-time data to reference data and provide an output signal in response to a comparison of the real-time data to the reference data. In embodiments, controller 4 can be configured to communicate with one or more of the motors 16 to adjust the position of tabs 18, 22, and/or an amount of tension in one or more of connector members 26 in response to the output signal. In some embodiments, controller 4 may be configured to check whether connector members 26 in surgical instrument 20, are associated with any previously stored reference conditions while surgical instrument 20 is coupled to one of robot arm 2, 3. Controller 4 may then be configured to retrieve the reference conditions form a memory to the extent that such as association exists, otherwise controller 4 may be configured to trigger one or more of the aforementioned procedures to generate and then store the reference condition. Once the reference condition has been generated and/or retrieved, controller 4 may be configured to further trigger, in response to one or more events, one or more of the aforementioned procedures to generate and/or store an updated condition of connector member 26. These events can include, for example, an initial and/or subsequent coupling of the surgical instrument 20 to the robot arm 2, 3; a use count of the surgical instrument 20 that exceeds a threshold value; a user initiated command; and/or an expiration of one or more time periods.

Figure 4B:
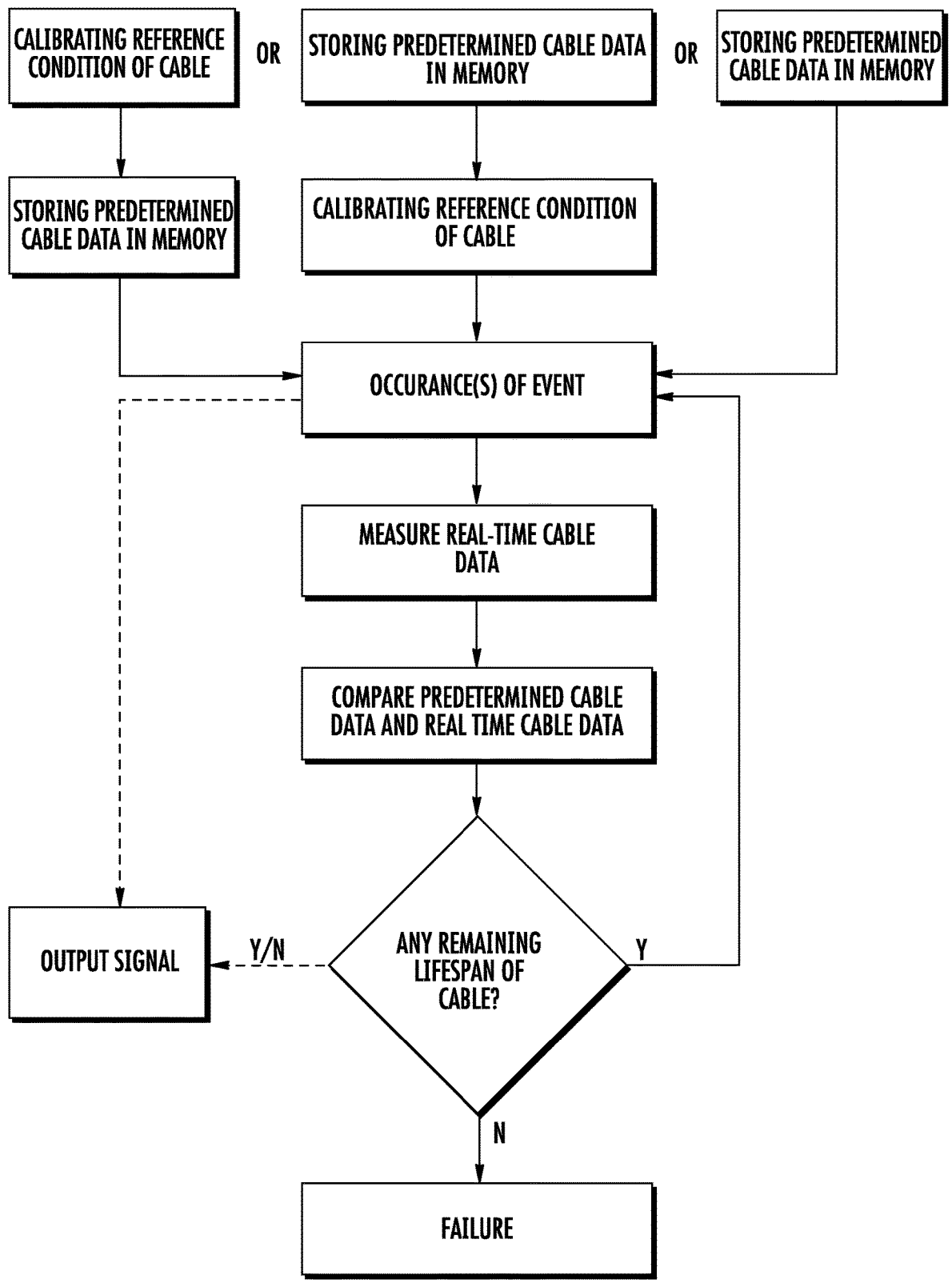
FIG. 4B is a flow chart illustrating a method for determining health of a connector member of a robotic surgical system.

In general, as illustrated in FIG. 4B, referenced data/information of the components of work station 1 (e.g., one or more connector members 26) can be stored in memory, for example, on a memory device coupled to medical work station 1 and/or part of remote system "RS" as described above. Such data/information can be stored prior to any use of one or more components of work station 1. One or more first events, such as those described above (e.g., generating and storing a reference or update condition, a use and/or a number of uses of one or more connector members 26), can occur so that real-time data of components of the work station 1 can be measured. Measurement of the real-time data can be determined by virtue of force and position sensors 19a, 19b and/or controller 4, prior to a use of one or more of the components.

In certain embodiments, reference data of the one or more connector members 26 can be compared with measured real-time data of the one or more connector members 26 to determine the real-time health (e.g., remaining/expended lifespan) of one or more connector members 26 relative to the initial health of one or more connector members 26. If lifespan/health of one or more of connector members 26 remains or is intact, an output signal may be provided. An occurrence of another event, which may be different and/or the same as the one or more first events, may also provide an output signal. If no health/lifespan remains or is otherwise registered/intact, there may be failure or an unusability of connector members 26, which can require adjustment and/or replacement of one or more of the components (e.g., connector members, end effector, etc.) of work station 1. The output signal can be any suitable signal, for example, indicative of health/remaining lifespan (e.g., via number of uses, time period, etc.), if any, and/or failure. An output signal indicative of failure can be generated by controller 4 upon a breaking of one or more of connector members 26, or upon a lengthening of the one or more connector members 26 beyond predetermined amount. As can be appreciated, stored pre-determined data may be preset and/or updated periodically, including before, during, and/or after use.

It is contemplated that methods of the present disclosure involve determine a tensile change in a connector member based on comparing a tension of connector member 26 with a position of a component coupled to connector member 26. In some embodiments, controller 4 can be configured to generate/analyze force versus position plots to approximate a degradation of connector member 26.

In some instances, the method may include initially calibrating a reference condition in connector member 26, but in other instances this feature may have been previously performed, calculated, or estimated. The method can include measuring the real-time data of the one or more connector members 26 after one or more uses thereof.

In certain embodiments, the method involves automating an output signal indicative of real-time data of the one or more connector members 26 in response to one or more events. The one or more events can include a first use of the surgical tool, a use of the surgical tool subsequent to the first use of the surgical tool, and/or an expiration of one or more time periods.

The method may include receiving an input signal, indicative of a user input, as an event to initiate an output signal indicative of real-time data of the one or more connector members 26. The method can involve registering a failure of the one or more connector members 26 and providing an output signal indicative of the failure.

Figure 5:
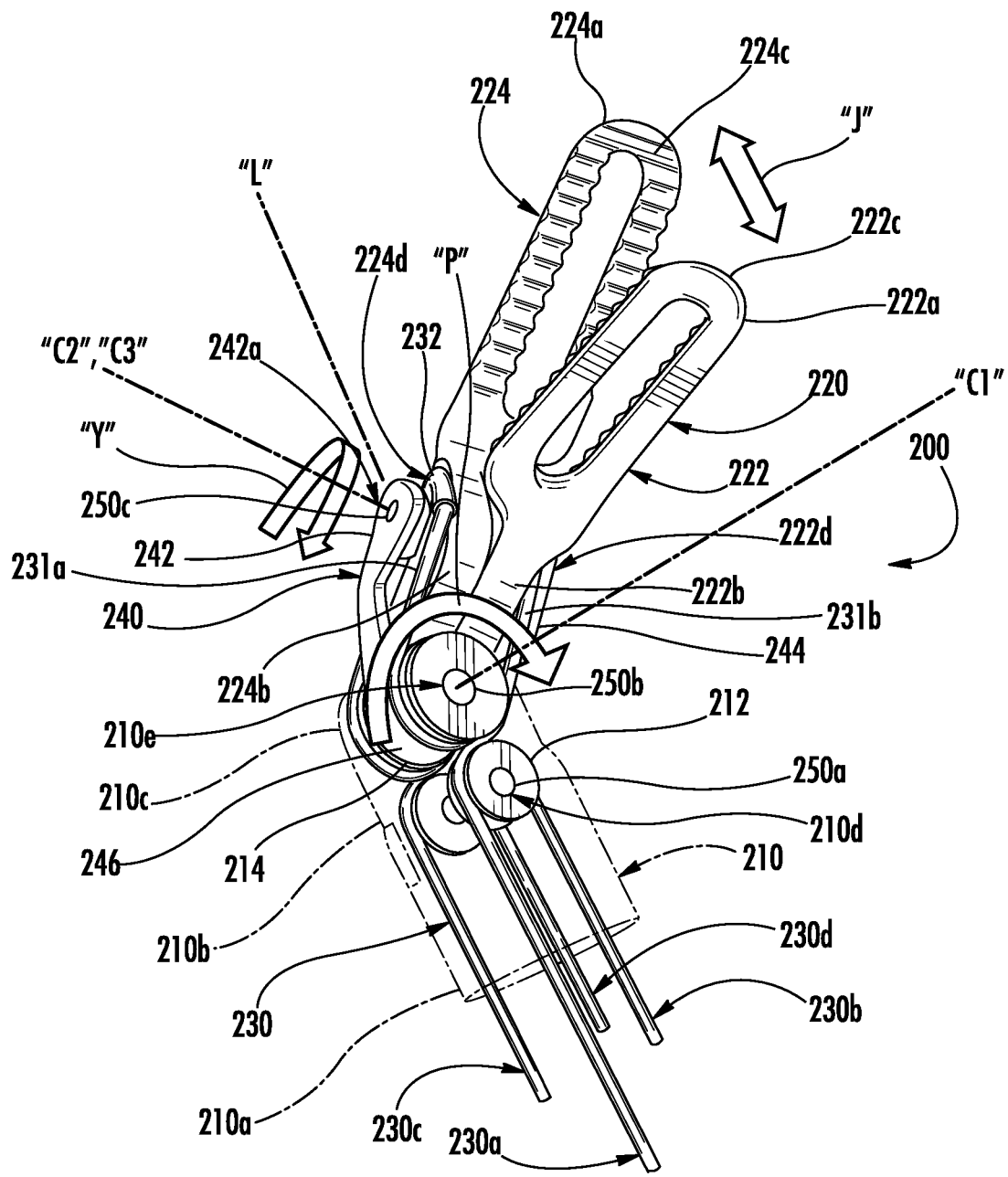
FIG. 5 is a perspective view of another embodiment of an end effector for use in the medical work station of FIG. 1A.
Figure 6A:
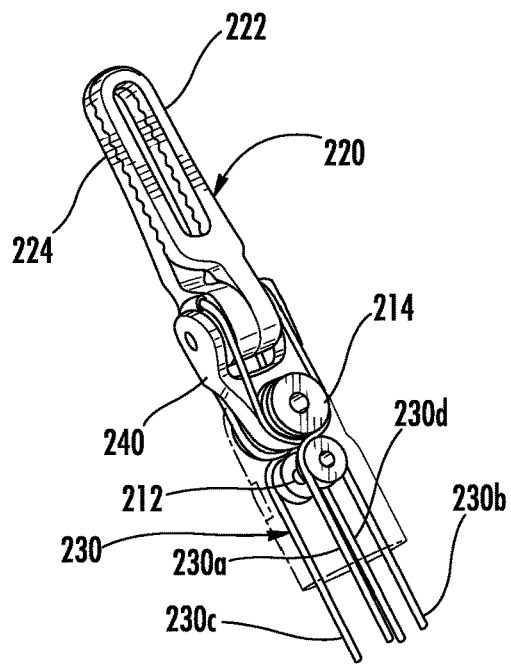
FIG. 6A is a perspective view of the end effector of FIG. 5 shown in a straight configuration with jaw members thereof in a closed configuration.
Figure 6B:
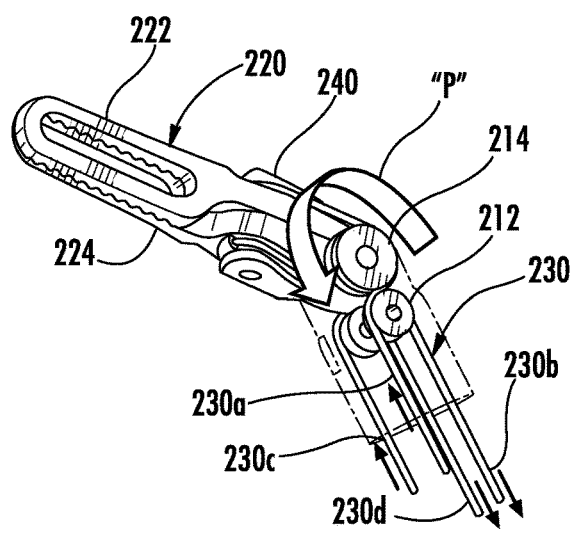
FIG. 6B is a perspective view of the end effector of FIG. 5 shown in a pitched configuration with the jaw members thereof in the closed configuration.
Figure 6C:
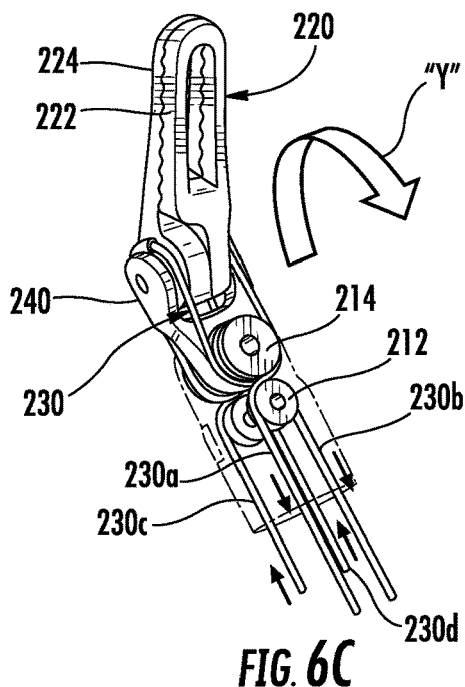
FIG. 6C is a perspective view of the end effector of FIG. 5 shown in a yawed configuration with the jaw members thereof in the closed configuration.
Figure 6D:
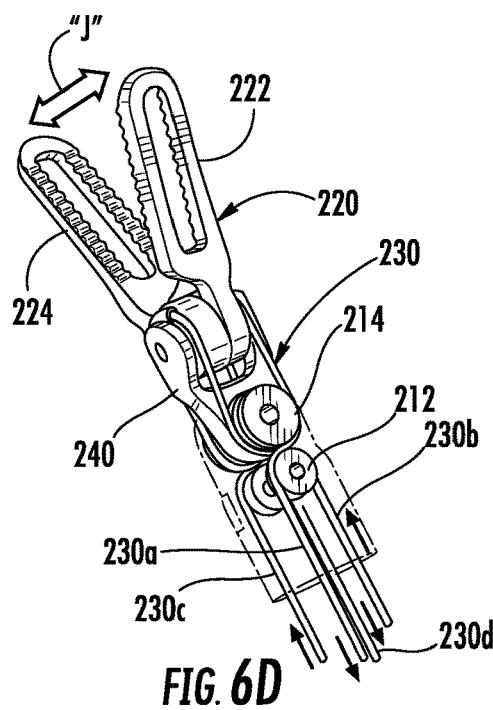
FIG. 6D is a perspective view of the end effector of FIG. 5 shown in the straight configuration with the jaw members thereof in an open configuration.

Turning now to FIG. 5, one embodiment of an end effector 200 for use in the medical work station 1 is illustrated. End effector 200 is a wristed surgical device that uses differential cable tension on four connector member ends 230a-230d of a pair of connector members 231a, 231b to drive three primary motion outputs: yawing movement, illustrated by arrow "Y," pitching movement, illustrated by arrow "P," and grasping movement, illustrated by arrow "J."

End effector 200 includes a mounting member or wrist assembly 210, a jaw assembly 220, a connector member assembly 230, and a clevis 240 that are operatively coupled to medical work station 1.

Wrist assembly 210, which may form part of shaft assembly 21 of surgical instrument 20, has a mount body 210a with a proximal end that couples to surgical instrument 20 (FIG. 1B). Mount body 210a extends distally to a pair of spaced-apart arms including a first arm 210b and a second arm 210c. The pair of spaced-apart arms defines a first pin channel 210d and a second pin channel 210e that extend transversely through each of first and second arms 210b, 210c. Wrist assembly 210 supports a first set of idler pulleys 212 and a second set of idler pulleys 214 that are aligned with first and second pin channels 210d, 210e, respectively, such that the first set of idler pulleys 212 is located proximal of second set of idler pulleys 214. First and second sets of idler pulleys 212, 214 are secured to wrist assembly 210 via first and second pulley pins 250a, 250b, respectively. Second pulley pin 250b and second set of idler pulleys 214 define a pitch axis "C1" about which first and second jaw members 222, 224 pitch relative to longitudinal axis "L."

Jaw assembly 220 includes a first jaw member 222 and a second jaw member 224 that are pivotably coupled together. First jaw member 222 includes a grasping portion 222a that extends distally from a jaw pulley 222b. Second jaw member 224 includes a grasping portion 224a that extends distally from a jaw pulley 224b. First and second jaw pulleys 222b, 224b may be integrally formed with grasping portions 222a, 224a, respectively. Grasping portions 222a, 224a include respective tissue-engaging surfaces 222c, 224c configured to engage tissue. First and second jaw pulleys 222b, 224b define respective first and second connector member channels 222d, 224d configured to receive connector member assembly 230.

Connector member assembly 230 includes a pair of connector members 231a, 231b that are routed/wrapped around the sets of idler pulleys 212, 214 and jaw pulleys 222b, 224b to a plurality of connector member portions 230a-230d. First connector member 231a of the pair of connector members 231a, 231b includes a first connector member portion 230a of the plurality of connector member portions 230a-230d at one end thereof and a second connector member portion 230c of the plurality of connector member portions 230a-230d at a second end thereof. Second connector member 231b of the pair of connector members 231a, 231b includes a third connector member portion 230b of the plurality of connector member portions 230a-230d at a first end thereof and a fourth connector member portion 230d of the plurality of connector member portions 230a-230d at a second end thereof. A plurality of ferrules 232 (only one being shown) are coupled to the pair of connector members 231a, 231b to secure the pair of connector members 231a, 231b to first and second jaw members 222, 224 of jaw assembly 220, respectively. A central portion of first connector member 231a is secured to jaw pulley 222b of first jaw member 222 by first one of the pair of ferrules 232 and a central portion of second connector member 231b is secured to jaw pulley 224b of second jaw member 224 by a second one of the pair of ferrules 232. Proximal ends of cable member portions 230a-230d are coupled to one or more instrument tabs 22 of surgical instrument 22 so that connector member portions 230a-230d move in response to movement of the instrument tabs 22 as described above.

For example, as seen in FIGS. 6A-6D, one or more of connector member portions 230a-230d can be moved independently of one or more of the other connector member portions 230a-230d and/or simultaneously with one or more of the other connector member portions 230a-230d in the same and/or in opposite directions of one or more of the other connector member portions 230a-230d to effectuate pitching, yawing, and/or opening/closing of jaw assembly 220.

With continued reference to FIGS. 5 and 6A-6D, clevis 240 includes a pair of fingers 242, 244 that extend from a base portion 246. Each of the pair of fingers 242, 244 is spaced apart from the other and together, the pair of fingers 242, 244 defines a pin passage 242a that extends therethrough. The base portion 246 is pivotally mounted to second set of idler pulleys 214 by pivot pin 250b to enable jaw assembly 220 to pitch/articulate, as indicated by arrow "P," relative to a longitudinal axis "L" of end effector 200. Jaw pulleys 222b, 224b of jaw assembly 220 are coupled together and mounted between the pair of fingers 242, 244 of clevis 240 by pivot pin 250c. Pivot pin 250c and jaw pulleys 222b, 224b of jaw assembly 220 define yaw and grasping axes "C2" and "C3," respectively, which are coincident with each other. Pin passage 242a receives pivot pin 250c to enable jaw assembly 220 to yaw about yaw axis "C2" relative to a longitudinal axis "L" of end effector 200, as indicated by arrow "Y," and/or open/close jaw assembly 220, about grasping axis "C3" as indicated by arrow "J." With this arrangement, wrist length is minimized, enabling greater pitch and/or yaw movement while minimizing shaft motion, which, in turn, enables multiple instruments to be placed closer together and/or enables faster manipulation of the end effector.

In use, the pair of connector members 231a, 231b, namely the plurality of connector member portions 230a-230d can be pulled and/or released by movement of instrument tabs 22, described above, to achieve pitch, yaw, grasping/dissecting and/or any combinations of these motions. This differential drive arrangement advantageously enables the tension in the pair of connector members 231a, 231b to be adjusted and/or relaxed as desired, for example, to limit load applied to various components of the surgical system (e.g., connector members, pulleys, tabs, etc.). Furthermore, position and/or force sensors 19a, 19b can be utilized to actively monitor output loads, such as grasping force, torque around the pitch axis, and torque around the yaw axis.

In a force feedback test performed in connection with an embodiment of end effector 200 with a four connector member differential arrangement (see, e.g., connector member portions 230a, 230b, 230c, and 230d), individual connector member tensions were monitored using a test rig with independent position control of each connector member portion to calculate forces at distal tips of a pair of jaw members (see, e.g., first and second jaw members 222, 224). The test rig included a custom jaw set of 17-4 H900 Direct Metal Laser sintered (DMLS) jaws with a load cell at the tip thereof to evaluate the feasibility of using connector member tensions of full length tungsten connector members to estimate tip grasping forces "F." Each jaw member of the jaw set included a jaw pulley. Each jaw pulley had the same radius.

Tip forces were then computed by averaging the forces acting on both jaw members of the jaw set using the following formulas:

force of first jaw member ("Jaw1") of the jaw set ("Jaw1Force")=[(T3−T1)×radius of one of the jaw pulleys]/length of one of the jaw members;

force of second jaw member ("Jaw2") of the jaw set ("Jaw2Force")=[(T4−T2)×radius of one of the jaw pulleys]/length of one of the jaw members; and calculated force=[Jaw1Force+Jaw2Force]/2;

where T1–T4 correspond to tension applied to connector member portions 230a-230d, respectively.

Figure 7A:
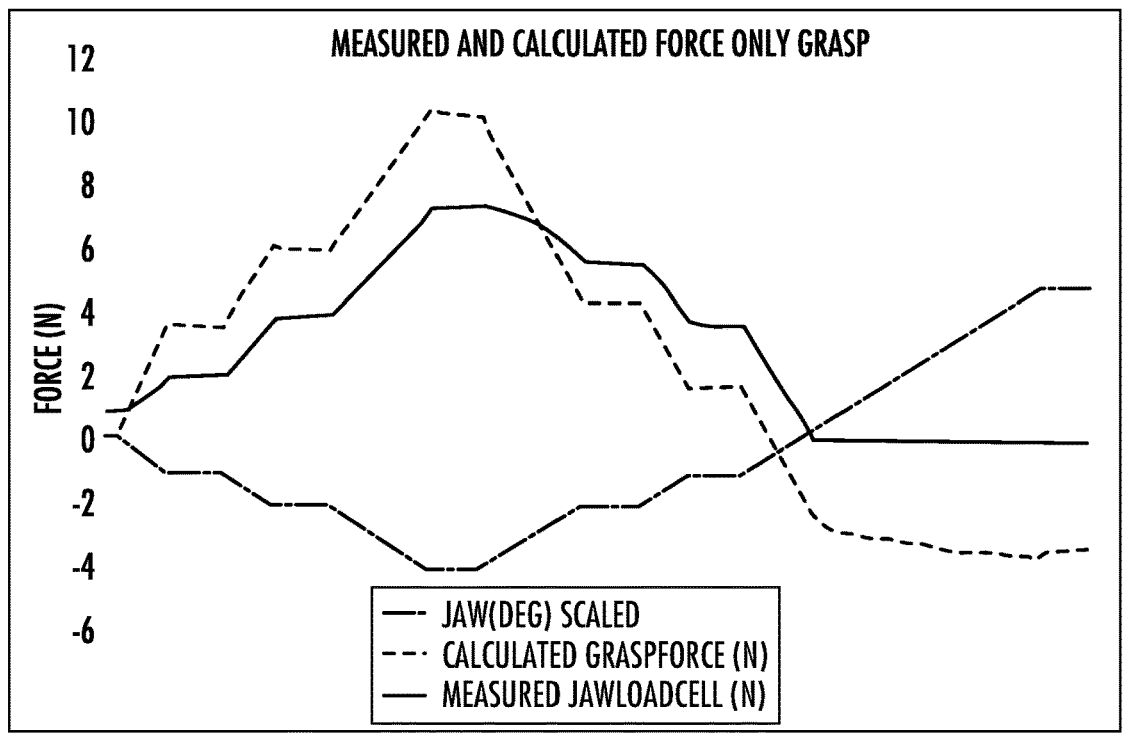
FIGS. 7A and 7B are graphical depictions of grasping force data established with respect to the end effector of FIG. 5.
Figure 7B:
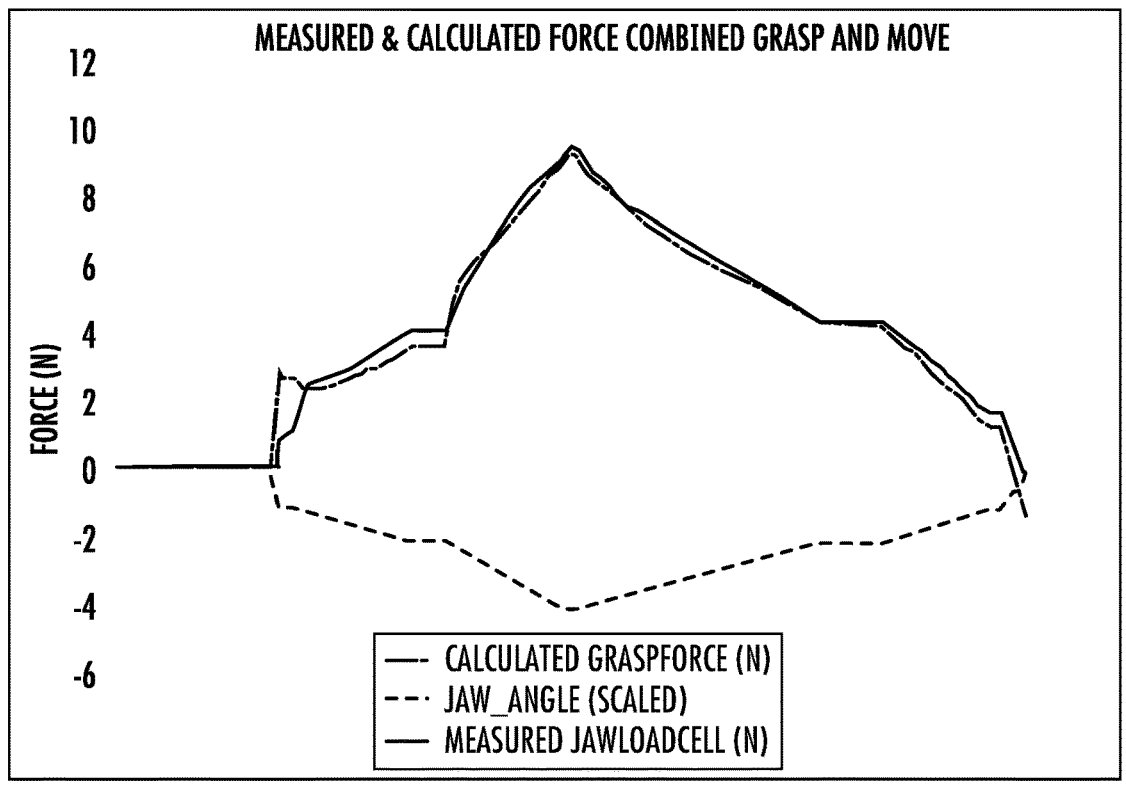

To simulate the presence of an external force, Jaw1 and Jaw2 were driven into each other to develop force data with respect to only the grasp (see FIG. 7A) and with respect to combined grasp and movement (see FIG. 7B). As seen in FIGS. 7A and 7B, after running cyclic tests while varying jaw, pitch, and yaw angles, the results were then plotted on a graph with respect to the calculated forces. Negative jaw angles indicated jaw overlap: the greater the negative value, the higher the simulated force. With respect to FIG. 7B, the graph indicates that the calculated grasping force tracts the measured jaw force with an increase in the grasping force as the jaw angle is decreased. FIG. 7A shows the measured versus calculated forces without any pitch and yaw motions as Jaw1 and Jaw2 are closed together. Even in this case, the calculated force tracks the measured force. There is a positive offset (calculated force is greater than measured force) when Jaw1 and Jaw2 are moving closer to each other (closing). This offset reverses when Jaw1 and Jaw2 start moving away from each other (opening). Once the jaw angle is greater than zero, there is no force recorded by the load cell.

The near perfect tracking of the calculated force shown in FIG. 7B as compared to the offsets in the calculated force shown in FIG. 7A can be explained by accounting for friction. In the test, the connector members were preloaded to 20 N to increase stiffness in the system. When Jaw1 and Jaw2 were driven into each other, the tensions rose up 120 N. This connector member tension pulled Jaw1 and Jaw2 into the pivot pin on which Jaw1 and Jaw2 rotate. The normal force between the pivot pin and Jaw1 and Jaw2 caused frictional force that opposed applied force. The direction of the frictional force changed depending on the direction of motion.

Therefore, in the absence of friction:

Jaw1Force=Jaw2Force

In the presence of friction:

Jaw1Force=F+f when Jaw1 is driven into Jaw2 BUT

Jaw1Force=F−f when Jaw1 is in contact with Jaw2 and is driven away from Jaw2

Similarly,

Jaw2Force=F+f when Jaw2 is driven into Jaw1 BUT

Jaw2Force=F−f when Jaw2 is in contact with Jaw1 and is driven away from Jaw1

Where the combination of yaw motion along with jaw closing causes Jaw 1 to move towards Jaw2 while Jaw 2 moves away from Jaw 1:

Jaw1Force=F+f and Jaw2Force=F−f

Computed Force=(Jaw1Force+Jaw2Force)/2=(F+f+F−f)/2=F

The error in measurement occurs when both Jaw1 and Jaw2 are moving towards each other or away from each other. The error is +/−f. This 2 f range of error can be observed in the plotted data as the difference between the observed and the measure (Max 3 N).

Although accuracy of measured force depends on the overall friction in the system, taking friction into account, measured and calculated forces track one another nearly perfectly in both of the plotted test cases, thereby evidencing the ability to estimate grasping forces by monitoring connector member tensions.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A method of determining health of at least one connector member of a robotic surgical system, the at least one connector member operably coupled to an end effector of the robotic surgical system and movable to operate the end effector, the method comprising:
   storing reference data of the at least one connector member prior to an initial use of the at least one connector member including an initial linear stretching distance of the at least one connector member, the at least one connector member having an initial health;
   measuring real-time data of the at least one connector member subsequent to the initial use of the at least one connector member including a subsequent linear stretching distance of the at least one connector member; and
   comparing the reference data of the at least one connector member with measured real-time data of the at least one connector member to determine a real-time health of the at least one connector member relative to the initial health of the at least one connector member.

2. The method of claim 1, wherein measuring real-time data of the at least one connector member includes measuring force applied to the at least one connector member.

3. The method of claim 1, further including calibrating tension in the at least one connector member in response to changes in the real-time data of the at least one connector member.

4. The method of claim 1, further including automating an output signal indicative of real-time data of the at least one connector member in response to at least one event.

5. The method of claim 1, further including receiving an input signal indicative of a user input to initiate an output signal indicative of real-time data of the at least one connector member.

6. The method of claim 1, further including registering a failure of the at least one connector member and providing an output signal indicative of the failure.

7. The method of claim 1, further including sending an alert indicating that the at least one connector member needs to be replaced.

\* \* \* \* \*